(12) United States Patent
Rölle et al.

(10) Patent No.: US 7,091,242 B2
(45) Date of Patent: Aug. 15, 2006

(54) BETA-AMINO ACID DERIVATIVES AS INTEGRIN RECEPTOR ANTAGONISTS

(75) Inventors: Thomas Rölle, Leverkusen (DE); Thomas Lehmann, Bergisch Gladbach (DE); Markus Albers, Leverkusen (DE); Gerhard Hessler, Hofheim (DE); Gerhard Müller, Krefeld (DE); Rüdiger Fischer, Pulheim (DE); Masaomi Tajimi, Kyoto (JP); Karl Ziegelbauer, Haan (DE); Kevin Bacon, Kobe (JP); Haruki Hasegawa, Ann Arbor, MI (US); Hiromi Okigami, Kyoto (JP)

(73) Assignee: Bayer Aktiengesellschaft, Leverkusen (DE)

( * ) Notice: Subject to any disclaimer, the term of this patent is extended or adjusted under 35 U.S.C. 154(b) by 81 days.

(21) Appl. No.: 10/398,267

(22) PCT Filed: Oct. 8, 2001

(86) PCT No.: PCT/EP01/11586

§ 371 (c)(1),
(2), (4) Date: Sep. 29, 2003

(87) PCT Pub. No.: WO02/30875

PCT Pub. Date: Apr. 18, 2002

(65) Prior Publication Data

US 2004/0058904 A1 Mar. 25, 2004

(30) Foreign Application Priority Data

Oct. 9, 2000 (GB) ................................. 0024693.4

(51) Int. Cl.
*A61K 31/21* (2006.01)
*C07C 69/00* (2006.01)
(52) U.S. Cl. .............................. 514/506; 560/2; 560/45

(58) Field of Classification Search .................. 560/21, 560/45; 514/506
See application file for complete search history.

(56) References Cited

U.S. PATENT DOCUMENTS

| 5,681,820 A | 10/1997 | Ruminski et al. ............. 514/18 |
| 2003/0216325 A1* | 11/2003 | Saksena et al. ............... 514/18 |

FOREIGN PATENT DOCUMENTS

| DE | 19962936 | 6/2001 |
| WO | 9619223 | 6/1996 |
| WO | 9926923 | 6/1999 |
| WO | 0000477 | 7/1999 |
| WO | 9933789 | 7/1999 |
| WO | 9937605 | 7/1999 |
| WO | 0000477 | 1/2000 |
| WO | 9937605 | 1/2000 |

OTHER PUBLICATIONS

Saksena et al., 2002, CAS: 139:381756.*
Bergel, F. et al., "Synthesis of Beta-(p-bis(2-chloroethyl)aminophenyl)-DL-Beta-alanine, a new amino acid derivative with tumour-inhibiting properties", Chem & Ind. pp. 1487 (1959).
Aberhart, D. et al., "Synthesis of Geometrical Isomers of Beta-Arylamidoacrylic Esters,". J. Org. Chem. 46, 3749-3751 (1981).
Johnson, J.M., "Synthesis of Beta(m-bis(2-Chloroethyl)aminophenyl)-DL-Beta-alanine", Chem & Ind., 966-967, (1960).

* cited by examiner

*Primary Examiner*—Joseph K. McKane
*Assistant Examiner*—Robert Shiao

(57) ABSTRACT

The present invention relates to compounds of the general formula (I), processes for their preparation, pharmaceutical compositions containing them as well as their use for the production of pharmaceutical compositions for the treatment of inflammatory diseases.

11 Claims, No Drawings

BETA-AMINO ACID DERIVATIVES AS INTEGRIN RECEPTOR ANTAGONISTS

This application is a 371 of PCT/EP01/11586 filed on Oct. 8, 2001, and claim benefit of UNITED KINGDOM 0024693.4 filed on Oct. 9, 2000.

The present invention relates to compounds of formula (I),

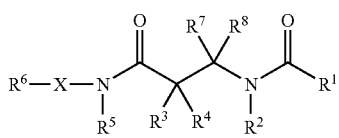

their preparation and use as pharmaceutical compositions as integrin antagonists, especially as $\alpha_4\beta_1$ and/or $\alpha_4\beta_7$ and/or $\alpha_9\beta_1$ integrin antagonists and in particular for the production of pharmaceutical compositions suitable for the inhibition or the prevention of cell adhesion and cell-adhesion mediated disorders.

Adhesive interactions between the leukocytes and endothelial cells play a critical role in leukocyte trafficking to sites of inflammation. These events are essential for normal host defense against pathogens and repair of tissue damage, but can also contribute to the pathology of a variety of inflammatory and autoimmune disorders. Indeed, eosinophil and T cell infiltration into the tissue is known as a cardinal feature of allergic inflammation such as asthma.

The interaction of circulating leukocytes with adhesion molecules on the luminal surface of blood vessels appears to modulate leukocyte transmigration. These vascular cell adhesion molecules arrest circulating leukocytes, thereby serving as the first step in their recruitment to infected or inflamed tissue sites. Subsequently, the leukocytes reaching the extravascular space interact with connective tissue cells such as fibroblasts as well as extracellular matrix proteins such as fibronectin, laminin, and collagen. Adhesion molecules on the leukocytes and on the vascular endothelium are hence essential to leukocyte migration and attractive therapeutic targets for intervention in many inflammatory disorders.

Leukocyte recruitment to sites of inflammation occurs in a stepwise fashion beginning with leukocyte tethering to the endothelial cells lining the blood vessels. This is followed by leukocyte rolling, activation, firm adhesion, and transmigration. A number of cell adhesion molecules involved in those four recruitment steps have been identified and characterized to date. Among them, the interaction between vascular cell adhesion molecule 1 (VCAM-1) and very late antigen 4 (VLA-4, $\alpha_4\beta_1$ integrin), as well as the interaction between mucosal addressin cell adhesion molecule 1 (MAdCAM-1) and $\alpha_4\beta_7$ integrin, has been shown to mediate the tethering, rolling, and adhesion of lymphocytes and eosinophils, but not neutrophils, to endothelial cells under a physiologic flow condition. This suggests that the VCAM-1/VLA-4 and/or MAdCAM-1/$\alpha_4\beta_7$ integrin mediated interactions could predominantly mediate a selective recruitment of leukocyte subpopulations in vivo. The inhibition of this interaction is a point of departure for therapeutic intervention (A. J. Wardlaw, *J. Allergy Clin. Immunol.* 1999, 104, 917–26).

VCAM-1 is a member of immunoglobulin (Ig) superfamily and is one of the key regulators of leukocyte trafficking to sites of inflammation. VCAM-1, along with intracellular adhesion molecule 1 (ICAM-1) and E-selectin, is expressed on inflamed endothelium activated by such cytokines as interleukin 1 (IL-1) and tumor necrosis factor $\alpha$ (TNF-$\alpha$), as well as by lipopolysaccharide (LPS), via nuclear factor $\kappa$B (NF-$\kappa$B) dependent pathway. However, these molecules are not expressed on resting endothelium. Cell adhesion mediated by VCAM-1 may be involved in numerous physiological and pathological processes including myogenesis, hematopoiesis, inflammatory reactions, and the development of autoimmune disorders. Integrins VLA-4 and $\alpha^4\beta_7$ both function as leukocyte receptors for VCAM-1.

The integrin $\alpha_4\beta_1$ is a heterodimeric protein expressed in substantial levels on all circulating leukocytes except mature neutrophils. It regulates cell migration into tissues during inflammatory responses and normal lymphocyte trafficking. VLA-4 binds to different primary sequence determinants, such as a QIDSP motif of VCAM-1 and an ILDVP sequence of the major cell type-specific adhesion site of the alternatively spliced type III connecting segment domain (CS-1) of fibronectin.

In vivo studies with neutralizing monoclonal antibodies and inhibitor peptides have demonstrated a critical role for $\alpha_4$ integrins interaction in leukocyte-mediated inflammation. Blocking of VLA-4/ligand interactions, thus, holds promise for therapeutic intervention in a variety of inflammatory, autoimmune and immune diseases (Zimmerman, C.; *Exp. Opin. Ther. Patents* 1999, 9, 129–133).

Furthermore, compounds containing a bisarylurea moiety as a substituent were disclosed as $\alpha_4\beta_1$ integrin receptor antagonists: WO 96/22966, WO 97/03094, WO99/20272, WO99/26923, WO 99/33789, WO 99/37605, WO 00/00477. However, no β-amino acids or homologues thereof with $\alpha_4\beta_1$ integrin receptor antagonistic activity have been described.

Further to their $\alpha_4\beta_1$ integrin antagonistic activity, the compounds of the present invention may also be used as $\alpha_4\beta_7$ or $\alpha_9\beta_1$ integrin antagonists.

An object of the present invention is to provide new β-amino acid or homologues thereof derived integrin antagonists for the treatment of inflammatory, autoimmune and immune diseases.

The present invention therefore relates to compounds of the general formula (I):

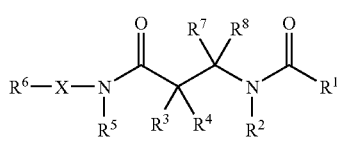

wherein $R^1$ represents a 4-to 9-membered saturated, unsaturated or aromatic cyclic residue,
   which can contain 0 to 3 heteroatoms selected independently from the group N, S and O,
   and wherein $R^1$ is substituted by —$R^{1-1}$—Z, wherein
$R^{1-1}$ represents a bond, —O—, —S—, $NR^{1-2}$, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 3 heteroatoms selected from the group oxygen, nitrogen or sulfur,
   wherein $R^{1-1}$ can optionally be substituted by 1 to 2 substituents selected from the group $R^{1-3}$, wherein $R^{1-2}$ can optionally be hydrogen, $C_1$–$C_{10}$ alkyl, $C_2$–$C_{10}$ alkenyl or $C_2$–$C_{10}$ alkynyl, and wherein $R^{1-3}$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 3 heteroatoms selected from the group oxygen, nitrogen or sulfur, Z represents —C(O)OR$^{Z-1}$, —C(O)NR$^{Z-2}$R$^{Z-3}$, —SO$_2$NR$^{Z-2}$R$^{Z-3}$, —SO(OR$^{Z-1}$), —SO$_2$(OR$^{Z-1}$), —P(O)R$^{Z-1}$(OR$^{Z-3}$) or —PO(OR$^{Z-1}$)(OR$^{Z-3}$), wherein $R^{Z-2}$ is hydrogen, $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl, —C(O)R$^{Z-4}$ or —SO$_2$R$^{Z-4}$, wherein $R^{Z-4}$ is $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl, $R^{Z-1}$ and $R^{Z-3}$ are independently selected from the group hydrogen, $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl or benzyl, wherein $R^{Z-1}$ and $R^{Z-3}$ can optionally be substituted by 1 to 3 substituents selected from the group $C_1$–$C_4$ alkyl, $C_1$–$C_4$ alkyloxy, halogen, nitro, cyano, and wherein $R^1$ can optionally be substituted by 0 to 2 substituents $R^{1-4}$, halogen, nitro, amino, cyano and oxo, wherein $R^{1-4}$ is selected from the group $C_1$–$C_4$ alkyl, $C_1$–$C_4$ alkyloxy, phenyl, phenoxy, phenylamino, $C_3$–$C_6$ cycloalkyl, $R^2$ represents hydrogen, $C_1$–$C_{10}$ alkyl, $C_2$–$C_{10}$ alkenyl, $C_2$–$C_{10}$ alkynyl, $C_6$ or $C_{10}$ aryl or $C_3$–$C_7$ cycloalkyl, wherein $R^2$ can optionally be substituted by 1 to 3 radicals independently selected from the group $C_1$–$C_4$ alkyl, trifluormethyl, trifluormethoxy, halogen, cyano, nitro or oxo, $R^3$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, wherein $R^3$ can optionally be substituted by 1 to 3 radicals $R^{3-1}$, wherein $R^{3-1}$ represents $C_1$–$C_4$ alkyl, trifluoroethyl, trifluormethoxy, —OR$^{3-2}$, —SR$^{3-2}$, NR$^{3-3}$R$^{3-4}$, —C(O)R$^{3-2}$, S(O)R$^{3-2}$, —SO$_2$R$^{3-2}$, —OC(O)R$^{3-2}$, —C(O)NR$^{3-3}$R$^{3-4}$, —NR$^{3-2}$C(O)R$^{3-3}$, —SO$_2$NR$^{3-3}$R$^{3-4}$, NR$^{3-2}$SO$_2$R$^{3-3}$, —NR$^{3-2}$C(O)NR$^{3-3}$R$^{3-4}$, —NR$^{3-2}$C(O)OR$^{3-3}$, —OC(O)NR$^{3-3}$R$^{3-4}$, —CO$_2$R$^{3-5}$, halogen, cyano, nitro or oxo, wherein $R^{3-2}$ represents hydrogen, $C_1$–$C_4$ alkyl, $C_3$–$C_6$ cycloalkyl, $C_6$ or $C_{10}$ aryl, wherein $R^{3-3}$ and $R^{3-4}$ are independently selected from the group hydrogen, $C_1$–$C_4$ alkyl, $C_3$–$C_6$ cycloalkyl, $C_6$ or $C_{10}$ aryl or benzyl, and wherein $R^{3-5}$ represents $C_1$–$C_4$ alkyl, $C_3$–$C_6$ cycloalkyl, $C_6$ or $C_{10}$ aryl, $R^4$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, wherein $R^4$ can optionally be substituted by 1 to 3 radicals $R^{4-1}$, wherein $R^{4-1}$ represents $C_1$–$C_4$ alkyl, trifluormethyl, trifluormethoxy, —OR$^{4-2}$, —SR$^{4-2}$, NR$^{4-3}$R$^{4-4}$, —C(O)R$^{4-2}$, S(O)R$^{4-2}$, —SO$_2$R$^{4-2}$, —OC(O)R$^{4-2}$, —C(O)NR$^{4-3}$R$^{4-4}$, —NR$^{4-2}$C(O)R$^{4-3}$, —SO$_2$NR$^{4-3}$R$^{4-4}$, NR$^{4-2}$SO$_2$R$^{4-3}$, —NR$^{4-2}$C(O)NR$^{4-3}$R$^{4-4}$, —NR$^{4-2}$C(O)OR$^{4-3}$, —OC(O)NR$^{4-3}$R$^{4-4}$, —CO$_2$R$^{4-5}$, halogen, cyano, nitro or oxo, wherein $R^{4-2}$ represents hydrogen, $C_1$–$C_4$ alkyl, $C_3$–$C_6$ cycloalkyl, $C_6$ or $C_{10}$ aryl, wherein $R^{4-3}$ and $R^{4-4}$ are independently selected from the group hydrogen, $C_1$–$C_4$ alkyl, $C_3$–$C_6$ cycloalkyl, $C_6$ or $C_{10}$ aryl or benzyl, and wherein $R^{4-5}$ represents $C_1$–$C_4$ alkyl, $C_3$–$C_6$ cycloalkyl, $C_6$ or $C_{10}$ aryl or $R^3$ and $R^4$ together with the carbon atom to which they are attached form a 4–7-membered saturated or unsaturated ring containing up to 2 heteroatoms selected from the group oxygen, nitrogen or sulfur, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo and which can be fused with a 3–7 membered homocyclic or heterocyclic, saturated, unsaturated or aromatic ring, $R^5$ represents hydrogen, $C_1$–$C_{10}$ alkyl, $C_2$–$C_{10}$ alkenyl, $C_2$–$C_{10}$ alkynyl, $C_6$ or $C_{10}$ aryl or $C_3$–$C_7$ cycloalkyl, wherein $R^5$ can optionally up to threefoldedly be substituted by $C_1$–$C_4$ alkyl, trifluormethyl, trifluormethoxy, halogen, cyano, nitro or oxo, $R^6$ represents phenyl or a 5- to 6-membered aromatic heterocyclic residue containing up to 3 heteroatoms independently selected from the group oxygen, nitrogen or sulfur, which is substituted by —NR$^{6-2}$C(O)NR$^{6-3}$R$^{6-4}$ or —NR$^{6-2}$C(S)NR$^{6-3}$R$^{6-4}$ and can furthermore optionally be substituted by halogen, wherein $R^{6-2}$ and $R^{6-3}$ are independently selected from the group hydrogen or $C_1$–$C_4$ alkyl, or together form a group

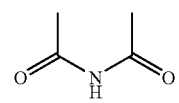

and wherein $R^{6-4}$ represents phenyl, wherein $R^{6-4}$ can optionally be substituted by 1–2 substituents selected from the group $C_1$–$C_4$ alkyl, $C_1$–$C_4$ alkyloxy, halogen, nitro, trifluoromethyl, trifluoromethoxy or cyano, $R^7$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, wherein $R^7$ can optionally be substituted by 1 to 3 radicals $R^{7-1}$, wherein $R^{7-1}$ represents $C_1$–$C_4$ alkyl, trifluormethyl, trifluormethoxy, —OR$^{7-2}$, —SR$^{7-2}$, NR$^{7-3}$R$^{7-4}$, —C(O)R$^{7-2}$, S(O)R$^{7-2}$, —SO$_2$R$^{7-2}$, —OC(O)R$^{7-2}$, —C(O)NR$^{7-3}$R$^{7-4}$, —NR$^{7-2}$C(O)R$^{7-3}$, —SO$_2$NR$^{7-3}$R$^{7-4}$, NR$^{7-2}$SO$_2$R$^{7-3}$, —NR$^{7-2}$C(O)NR$^{7-3}$R$^{7-4}$, —NR$^{7-2}$C(O)OR$^{7-3}$, —OC(O)NR$^{7-3}$R$^{7-4}$, —CO$_2$R$^{7-5}$, halogen, cyano, nitro or oxo, wherein $R^{7-2}$ represents hydrogen, $C_1$–$C_4$ alkyl, $C_3$–$C_6$ cycloalkyl, $C_6$ or $C_{10}$ aryl, wherein $R^{7-3}$ and $R^{7-4}$ are independently selected from the group hydrogen, $C_1$–$C_4$ alkyl, $C_3$–$C_6$ cycloalkyl, $C_6$ or $C_{10}$ aryl or benzyl, and wherein $R^{7-5}$ represents $C_1$–$C_4$ alkyl, $C_3$–$C_6$ cycloalkyl, $C_6$ or $C_{10}$ aryl $R^8$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, wherein $R^8$ can optionally be substituted by 1 to 3 radicals $R^{8-1}$, wherein $R^{8-1}$ represents $C_1$–$C_4$ alkyl, trifluormethyl, trifluormethoxy, —$OR^{8-2}$, —$SR^{8-2}$, $NR^{8-3}R^{8-4}$, —C(O)$R^{8-2}$, $S(O)R^{8-2}$, —$SO_2R^{8-2}$, —$OC(O)R^{8-2}$, —C(O)$NR^{8-3}R^{8-4}$, —$NR^{8-2}C(O)R^{8-3}$, —$SO_2NR^{8-3}R^{8-4}$, $NR^{8-2}SO_2R^{8-3}$, —$NR^{8-2}C(O)NR^{8-3}R^{8-4}$, —$NR^{8-2}C(O)OR^{8-3}$, —$OC(O)NR^{8-3}R^{8-4}$, —$CO_2R^{8-5}$, halogen, cyano, nitro or oxo, wherein $R^{8-2}$ represents hydrogen, $C_1$–$C_4$ alkyl, $C_3$–$C_6$ cycloalkyl, $C_6$ or $C_{10}$ aryl, wherein $R^{8-3}$ and $R^{8-4}$ are independently selected from the group hydrogen, $C_1$–$C_4$ alkyl, $C_3$–$C_6$ cycloalkyl, $C_6$ or $C_{10}$ aryl or benzyl, and wherein $R^{8-5}$ represents $C_1$–$C_4$ alkyl, $C_3$–$C_6$ cycloalkyl, $C_6$ or $C_{10}$ aryl or $R^7$ and $R^8$ together form a 4–7-membered saturated or unsaturated ring containing up to 2 heteroatoms selected from the group oxygen, nitrogen or sulfur, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo and which can be fused with a 3–7 membered homocyclic or heterocyclic, saturated, unsaturated or aromatic ring, X represents bond or (—$CR^{X-1}R^{X-2}$)$_n$, wherein $R^{X-1}$ and $R^{X-2}$ can be independently selected from the group hydrogen, $C_1$–$C_4$ alkyl, $C_2$–$C_4$ alkenyl, $C_2$–$C_4$ alkynyl, wherein $R^{X-1}$ and $R^{X-2}$ can optionally independently be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo, and wherein n is an integer 0 or 1, and pharmaceutically acceptable salts thereof.

In the context of the present invention alkyl stands for a straight-chain or branched alkyl residue, such as methyl, ethyl, n-propyl, iso-propyl, n-pentyl. If not stated otherwise, preferred is $C_1$–$C_{10}$ alkyl, very preferred is $C_1$–$C_6$ alkyl.

Alkenyl and alkinyl stand for straight-chain or branched residues containing one or more double or triple bonds, e.g. vinyl, allyl, isopropinyl, ethinyl. If not stated otherwise, preferred is $C_1$–$C_{10}$ alkenyl or alkinyl, very preferred is $C_1$–$C_6$ alkenyl or alkinyl.

Cycloalkyl stands for a cyclic alkyl group such as cyclopropyl, cyclobutyl, cyclopentyl, cyclohexyl or cycloheptyl. Preferred is monocyclic $C_3$–$C_7$ cycloalkyl.

Halogen in the context of the present invention stands for fluorine, chlorine, bromine or iodine. If not specified otherwise, chlorine or fluorine are preferred.

Homocycle stands for a ring consisting of carbon atoms.

A 4- to 9-membered saturated, unsaturated or aromatic cyclic residue stands for a monocyclic system containing 4 to 9 ring atoms and containing 0, 1 or more double bonds, which can be attached via a carbon atom or eventually via a heteroatom within the ring, for example phenyl, thiazolyl, pyridyl, cyclopentyl.

Aryl stands for a monocyclic Hueckel-aromatic cyclic system containing 6 or 10 ring carbon atoms.

Heteroaryl stands for a monocyclic heteroaromatic system containing 4 to 9 ring atoms, which can be attached via a carbon atom or eventually via a nitrogen atom within the ring, for example, furan-2-yl, furan-3-yl, pyrrol-1-yl, pyrrol-2-yl, pyrrol-3-yl, thienyl, thiazolyl, oxazolyl, imidazolyl, triazolyl, tetrazolyl, pyridyl, pyrimidyl or pyridazinyl.

A saturated or unsaturated heterocyclic residue stands for a heterocyclic system containing 4 to 9 ring atoms, which can contain one or more double bonds and which can be attached via a ring carbon atom or eventually via a nitrogen atom, e.g. tetrahydrofur-2-yl, pyrrolidine-1-yl, piperidine-1-yl, piperidine-2-yl, piperidine-3-yl, piperidine-4-yl, piperazine-1-yl, piperazine-2-yl morpholine-1-yl, 1,4-diazepine-1-yl or 1,4-dihydropyridine-1-yl.

If not specified otherwise, in the context of the present invention heteroatom stands preferably for O, S, N or P.

In a preferred embodiment, the present invention relates to compounds of general formula (I), wherein $R^1$ represents a phenyl ring.

In another preferred embodiment, the present invention relates to compounds of general formula (I), wherein $R^{1-1}$ represents a bond and Z represents COOR$^{Z-1}$, wherein $R^{Z-1}$ has the meaning indicated above.

In yet another preferred embodiment, the present invention relates to compounds of general formula (I), wherein $R^6$ represents phenyl, which is substituted by —NHC(O)NHR$^{6-4}$, wherein $R^{6-4}$ is substituted with methyl or trifluoromethoxy.

In yet another preferred embodiment, the present invention relates to compounds of general formula (I), wherein $R^{X-1}$ and $R^{X-2}$ represent hydrogen.

In yet another preferred embodiment, the present invention relates to compounds of general formula (I), wherein $R^3$ and $R^4$ together form a 6-membered homocycle.

In yet another preferred embodiment, the present invention relates to compounds of general formula (I), wherein $R^3$, $R^4$ and $R^7$ represent hydrogen and $R^8$ represents a 3-methoxyphenylradical or a 3,4-dimethoxyphenylradical.

In yet another preferred embodiment, the present invention relates to compounds of general formula (I), wherein $R^1$ is a 1,4-substituted phenyl ring.

Particularily preferred are the following compounds:

4-{[(1-(3,4-Dimethoxyphenyl)-3-{[4-({[(2-methylphenyl)amino]carbonyl}amino)phenyl]amino}-3-oxopropyl)amino]carbonyl}benzoic acid 4-[({[1-({[4-({[(2-Methylphenyl)amino]carbonyl}amino)benzyl]amino}carbonyl)cyclohexyl]methyl}amino)carbonyl]benzoic acid 4-{[(1-(3,4-Dimethoxyphenyl)-3-{[4-({[(2-methylphenyl)amino]carbonyl}amino)benzyl]amino}-3-oxopropyl)amino]caronyl}benzoic acid 4-{[(1-(3-Methoxyphenyl)-3-{[4-({[(2-methylphenyl)amino]carbonyl}amino)phenyl]amino}-3-oxopropyl)amino]caronyl}benzoic acid and their respective tert-butyl-benzoates.

A preferred process for preparation of compounds of general formula (I) has also been found, which comprises reaction of carboxylic acids of general formula (I')

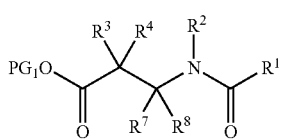

or activated derivatives thereof, with compounds of the general formula (I")

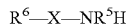

in inert solvents, which will be described in more detail in the descriptive part of the specification.

The intermediates (I'), wherein $R^1$, $R^2$, $R^3$, $R^4$, $R^7$ and $R^8$ have the abovementioned meaning and $PG_1$ represents a protecting group for the carboxyl group are also part of the present invention.

Surprisingly, the compounds of the present invention show good integrin antagonistic activity. They are therefore suitable for the treatment of diseases, especially as $\alpha_4\beta_1$, and/or $\alpha_4\beta_7$ and/or $\alpha_9\beta_1$ integrin antagonists and in the manufacture of a medicament for the treatment or the prevention of a condition mediated by-integrins and in particular for the production of pharmaceutical compositions for the inhibition or the prevention of cell adhesion and cell-adhesion mediated disorders. Examples are the treatment and the prophylaxis of atherosclerosis, asthma, chronic obstructive pulmonary disease (COPD), allergies, diabetes, inflammatory bowel disease, multiple sclerosis, myocardial ischemia, rheumatoid arthritis, transplant rejection and other inflammatory, autoimmune and immune disorders.

The integrin antagonists of the invention are useful not only for treatment of the physiological conditions discussed above, but are also useful in such activities as purification of integrins and testing for activity.

For the treatment of the above-mentioned diseases, the compounds according to the invention can exhibit non-systemic or systemic activity, wherein the latter is preferred. To obtain systemic activity the active compounds can be administered, among other things, orally or parenterally, wherein oral administration is preferred.

For parenteral administration, forms of administration to the mucous membranes (i.e. buccal, lingual, sublingual, rectal, nasal, pulmonary, conjunctival or intravaginal) or into the interior of the body are particularly suitable. Administration can be carried out by avoiding absorption (i.e. intracardiac, intra-arterial, intravenous, intraspinal or intralumbar administration) or by including absorption (i.e. intracutaneous, subcutaneous, percutaneous, intramuscular or intraperitoneal administration).

For the above purpose the active compounds can be administered per se or in administration forms.

Suitable administration forms for oral administration are, inter alia, normal and enteric-coated tablets, capsules, coated tablets, pills, granules, pellets, powders, solid and liquid aerosols, syrups, emulsions, suspensions and solutions. Suitable administration forms for parenteral administration are injection and infusion solutions.

The active compound can be present in the administration forms in concentrations of from 0.001–100% by weight; preferably the concentration of the active compound should be 0.5–90% by weight, i.e. quantities which are sufficient to allow the specified range of dosage.

The active compounds can be converted in the known manner into the abovementioned administration forms using inert non-toxic pharmaceutically suitable auxiliaries, such as for example excipients, solvents, vehicles, emulsifiers and/or dispersants.

The following auxiliaries can be mentioned as examples: water, solid excipients such as ground natural or synthetic minerals (e.g. talcum or silicates), sugar (e.g. lactose), non-toxic organic solvents such as paraffins, vegetable oils (e.g. sesame oil), alcohols (e.g. ethanol, glycerol), glycols (e.g. polyethylene glycol), emulsifying agents, dispersants (e.g. polyvinylpyrrolidone) and lubricants (e.g. magnesium sulphate).

In the case of oral administration tablets can of course also contain additives such as sodium citrate as well as additives such as starch, gelatin and the like. Flavour enhancers or colorants can also be added to aqueous preparations for oral administration.

For the obtainment of effective results in the case of parenteral administration it has generally proven advantageous to administer quantities of about 0.001 to 100 mg/kg, preferably about 0.01 to 1 mg/kg of body weight. In the case of oral administration the quantity is about 0.01 to 100 mg/kg, preferably about 0.1 to 10 mg/kg of body weight.

It may nevertheless be necessary to use quantities other than those mentioned above, depending on the body weight concerned, the method of administration, the individual response to the active compound, the type of preparation and the time or interval of administration.

Pharmaceutically acceptable salts of the compounds of the present invention that contain an acidic moiety include addition salts formed with organic or inorganic bases. The salt forming ion derived from such bases can be metal ions, e.g., aluminum, alkali metal ions, such as sodium of potassium, alkaline earth metal ions such as calcium or magnesium, or an amine salt ion, of which a number are known for this purpose. Examples include ammonium salts, arylalkylamines such as dibenzylamine and N,N-dibenzylethylenediamine, lower alkylamines such as methylamine, t-butylamine, procaine, lower alkylpiperidines such as N-ethylpiperidine, cycloalkyl-amines such as cyclohexylamine or dicyclohexylamine, 1-adamantylamine, benzathine, or salts derived from amino acids like arginine, lysine or the like. The physiologically acceptable salts such as the sodium or potassium salts and the amino acid salts can be used medicinally as described below and are preferred.

Pharmaceutically acceptable salts of the compounds of the present invention that contain a basic moiety include addition salts formed with organic or inorganic acids. The salt forming ion derived from such acids can be halide ions or ions of natural or unnatural carboxylic or sulfonic acids, of which a number are known for this purpose. Examples include chlorides, acetates, trifluoroacetates, tartrates, or salts derived from amino acids like glycine or the like. The physiologically acceptable salts such as the chloride salts, the trifluoroacetic acid salts and the amino acid salts can be used medicinally as described below and are preferred.

These and other salts which are not necessarily physiologically acceptable are useful in isolating or purifying a product acceptable for the purposes described below.

The compounds according to the invention can exist in different stereoisomeric forms, which relate to each other in an enantiomeric way (image and mirror image) or in a diastereomeric way (image different from mirror image). The invention relates to the enantiomers and the diastereomers as well as their mixtures. They can be separated according to customary methods.

General Compound Synthesis

The synthesis of compounds according to the general formula (I) can be illustrated by the following scheme 1:

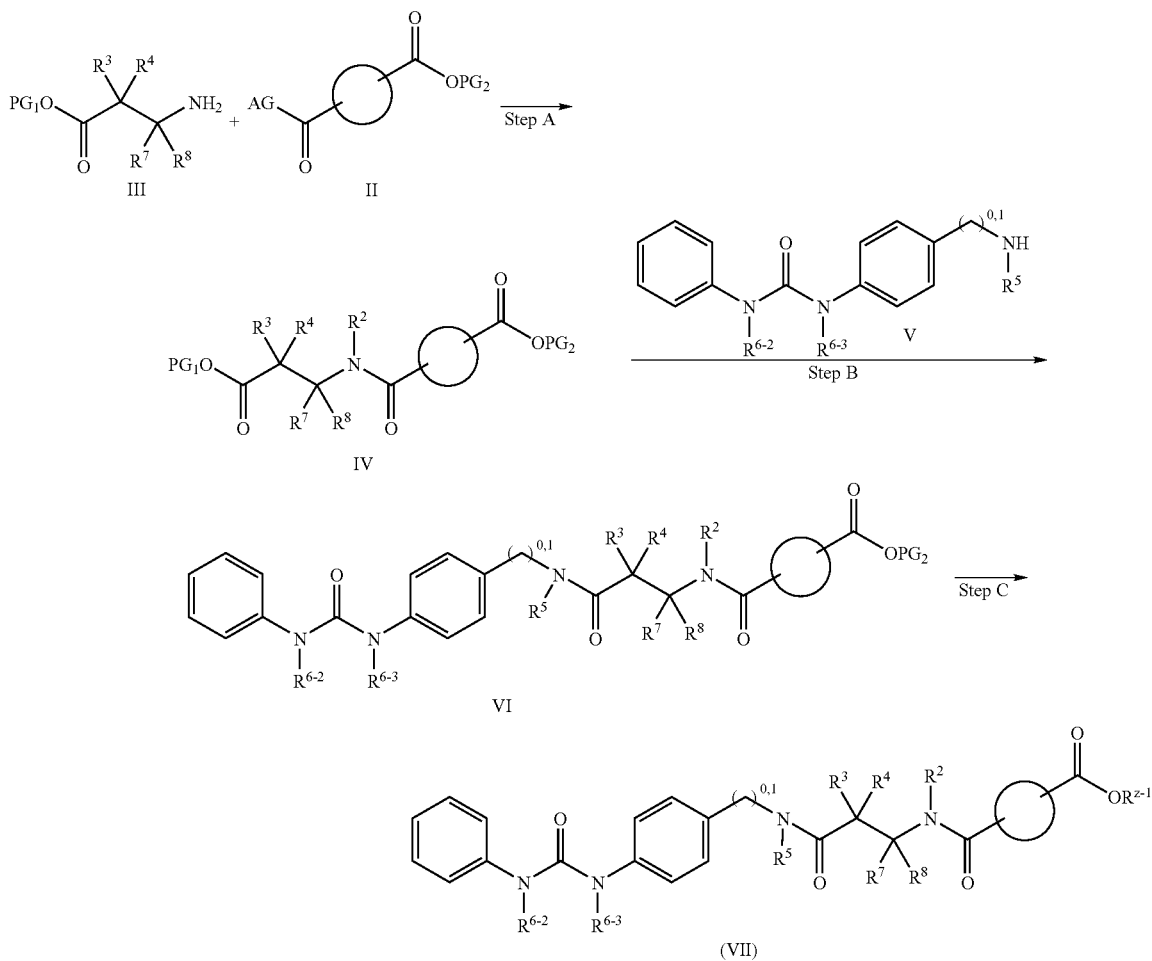

By coupling of the carboxylic acid derivatives (II) with the amines (III), the amides (IV) can be obtained. Removal of the protecting group $PG^1$ followed by coupling with the amines (V) yields the amides (VI). If a protecting group $PG_2$ is used, the removal of the latter affords carboxylic acids of type (VII).

In the above scheme the depicted ring in formulas (I), (II), (IV), and (VI) represents a cyclic moiety formed by $R^1$. AG stands for hydroxyl or a suitable activating group forming an activated carboxylic acid derivative. Activated carboxylic acids derivatives of this type are known to the person skilled in the art and are described in detail in standard textbooks such as, for example in (i) Houben-Weyl, Methoden der organischen Chemie [Methods of Organic Chemistry], Georg Thieme Verlag, Stuttgart or (ii) Comprehensive Organic Synthesis, Ed. B. M. Trost, Pergamon Press, Oxford, 1991. The carboxylic acid is preferably activated as, such as, for example, AG=1-hydroxy-1H-benzotriazol and a coupling agents such as, for example, dicyclohexylcarbodimid (DCC), 1-ethyl-3-(3'-dimethylaminopropyl)carbodiimide×HCl (EDCI), 2-(7-aza-3-oxido-1H-1,2,3-benzotriazol-1-yl)-1,1,3,3-tetramethyluronium hexafluorophosphate. Other activated carboxylic acid derivatives such as, for example symmetric anhydrides, mixed anhydrides, N-carboxy anhydrides, halides, or further activated esters e.g. succinyl or pentafluorophenyl esters may also be employed.

In the above scheme $PG^1$ and/or $PG^2$ stand for a suitable protecting group of the carboxyl group or $COOPG^1$ and/or $COOPG^2$ stand for the carboxylic group attached to a polymeric resin suitable for solid phase synthesis. Protecting groups of this type are known to the person skilled in the art and are described in detail in T. W. Greene, P. G. Wuts, *Protective Groups in Organic Synthesis*, $3^{rd}$ ed., John Wiley, New York, 1999. The carboxyl group is preferably esterified, $PG^1$ being $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclopropylmethyl, cyclobutyl, cyclopentyl, cyclohexyl, an aryl such as, for example, phenyl, benzyl, tolyl or a substituted derivative thereof.

Step A

Formation of the amides (IV) can take place by reacting an activated form of the respective carboxylic acid (II), such as a 1-hydroxy-1H-benzotriazol ester with the desired amine (III) or an acceptable salt thereof. 1-Hydroxy-1H-benzotriazol ester of (II) can be prepared, for example, by the reaction of the 1-hydroxy-1H-benzbtriazol with the carboxylic acids (II) in presence of an coupling agents such as, for example, dicyclohexylcarbodiimid (DCC), 1-ethyl-3-(3'-dimethylaminopropyl)carbodiimide×HCl (EDCI), 2-(7-aza-3-oxido-1H-1,2,3-benzotriazol-1-yl)-1,1,3,3-tetramethyluronium hexafluorophosphate. Further activated derivatives of the acids (II) such as other anhydrides, halides, esters e.g. succinyl or pentafluorophenyl esters or activated carboxylic acids obtained by the reaction with may also be employed.

For example, amides of type (IV) can be prepared as follows:

1-Hydroxy-1H-Benzotriazol Ester Procedure:

A solution of carboxylic acid, 1-hydroxy-1H-benzotriazol (HOBt) and 1-ethyl-3-(3'-dimethylaminopropyl) carbodiimide×HCl (EDCI) in an inert solvent is stirred at r.t. After addition of the amine and a non-nucleophilic base such as ethyldiisopropyl-amine or potassium carbonate stirring is continued at r.t. or elevated temperature. After evaporation, the residue was redissolved in ethyl acetate, washed with aqueous acid and base, dried and evaporated. If necessary the product was purified by trituration or by flash-chromatography or used without further purification.

Compounds of general formula (II) are commercially available, known or can be prepared by customary methods starting from commercially available precursors.

Compounds of general formula (III) are commercially available, known or can be prepared by customary methods starting from known carboxylic acid derivatives.

Step B

The removal of the protecting group $PG^1$ can be performed either by an acid such as trifluoroacetic acid or an base such as potassium hydroxide or lithium hydroxide, depending on the nature of $PG^1$. Reactions are carried out in aqueous, inert organic solvents such as alcohols e.g. methanol or ethanol, ethers e.g. tetrahydrofurane or dioxane or polar aprotic solvents e.g. dimethylformamide. If necessary, mixtures of the above solvents may be used.

Formation of the amides (VI) can take place by reacting the respective carboxylic acids (IV)-activated by a coupling agent such as DCC and HOBt; EDCI and HOBt or HATU—with the desired amines (V) or an acceptable salt thereof. Activated derivatives of the acids (IV) such as anhydrides, halides, and esters e.g. succinyl or pentafluorophenyl esters may also be employed.

For example, amides (VI) can be prepared as follows:

A solution of carboxylic acid, 1-hydroxy-1H-benzotriazol (HOBt) and 1-ethyl-3-(3'-dimethylaminopropyl) carbodiimide×HCl (EDCI) in an inert solvent is stirred at r.t. After addition of the amine and a non-nucleophilic base such as ethyldiisopropyl-amine or potassium carbonate stirring is continued at r.t. or elevated temperature. After evaporation, the residue was redissolved in ethyl acetate, washed with aqueous acid and base, dried and evaporated. If necessary the product was purified by trituration or by flash-chromatography or used without further purification.

Compounds of general formula (V) are commercially available, known or can be prepared by customary methods starting from known carboxylic acid derivatives. Bisaryl-lureas can be prepared by coupling of an amino phenyl acetic acid derivative and a phenylisocyanate.

Step C

The removal of the protecting group $PG^2$ can be performed either by an acid such as trifluoroacetic acid or an base such as potassium hydroxide or lithium hydroxide, depending on the nature of $PG^2$. Reactions are carried out in aqueous, inert organic solvents such as alcohols e.g. methanol or ethanol, ethers e.g. tetrahydrofurane or dioxane or polar aprotic solvents e.g. dimethylformamide. If necessary, mixtures of the above solvents may be used.

EXAMPLES

| Abbreviations | |
|---|---|
| AcOH | acetic acid |
| Boc | tert-butyloxycarbonyl |
| DCC | dicyclohexylcarbodiimid |
| DCM | dichloromethane |
| DIPEA | diisopropylethylamine |
| EDCI | 1-ethyl-3-(3'-dimethylaminopropyl)carbodiimidexHCl |
| eq. | equivalents |
| EtOAc | ethyl acetate |
| FC | flash chromatography |
| GC | gas chromatography |
| HATU | 2-(7-aza-3-oxido-1H-1,2,3-benzotriazol-1-yl)-1,1,3,3-tetramethyluronium hexafluorophosphate |
| HOBt | N-hydroxybenzotriazole monohydrate |
| HPLC | high performance liquid chromatography |
| ICAM-1 | intracellular adhesion molecule 1 |
| IL-1 | interleukin 1 |
| LPS | lipopolysaccharide |
| MAdCAM-1 | mucosal addressin cell adhesion molecule 1 |
| MeOH | methanol |
| MeCN | acetonitril |
| min. | minutes |
| M.p. | melting point |
| NE-κB | nuclear factor κB |
| NMR | nuclear magnetic resonance |
| n.d. | not determined |
| PE | light petroleum (b.p. 40–60° C.) |
| r.t. | room temperature |
| $R_f$ | TLC: $R_f$ value = distance spot traveled/distance solvent front traveled |
| TFA | trifluoroacetic acid |
| THF | tetrahydrofurane |
| TLC | thin layer chromatography |
| TNF-α | tumor necrosis factor α |
| $t_R$ | retention time determined by HPLC |
| VCAM-1 | vascular cell adhesion molecule 1 |
| VLA-4 | very late antigen 4 ($α_4β_1$ integrin) |

General Remarks

In the examples below, all quantitative data, if not stated otherwise, relate to percentages by weight.

Flash chromatography was carried out on silica gel 60, 40–63 μm. (E. Merck, Darmstadt, Germany).

Thin layer chromatography was carried out, employing silica gel 60 $F_{254}$ coated aluminum sheets (E. Merck, Darmstadt, Germany) with the mobile phase indicated.

Melting points were determined in open capillaries and are not corrected.

The mass determinations were carried out using the electron spray ionization (ESI) method employing loop injection or split injection via a HPLC system.

Precursor Synthesis

Example I

N-(4-Aminophenyl)-N'-(2-methylphenyl)urea

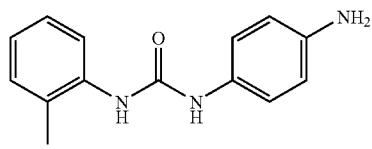

2-Methylphenylisocyanate (24.6 g, 184.9 mmol) was added dropwise at 0° C. to a solution of 1,4-diamino benzene (20.00 g, 184.9 mmol) in 1000 mL EtOAc. After stirring for 2 h at r.t. the product was collected by filtration (42.7 g, 177.0 mmol). M.p. >300° C.;

TLC (PE/EtOAc 1/4) $R_f$ 0.32; $^1$H-NMR (400 MHz, D$_6$-DMSO) δ2.10 (s, 3H); 4.76 (s, 2H); 6.59 (mc, 2H); 6.89 (mc, 1H); 7.07–7.15 (m, 4H); 7.73 (s, 1H); 7.85 (mc, 2H); 8.50 (s, 1H).

Example II tert-Butyl 4-({[(2-methylphenyl)amino]carbonyl}amino)benzyl-carbamate

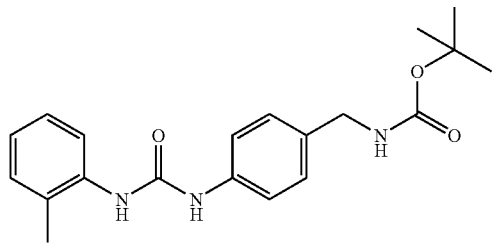

2-Methylphenylisocyanate (7.57 g, 59.83 mmol) was added dropwise at 0° C. to a solution of (4-amino-benzyl)-carbamic acid tert-butyl ester (13.30 g, 59.83 mmol, prepared analoguous to: Moloney, Gerard P.; Martin, Graeme R.; Mathews, Neil; Milne, Aynsley; Hobbs, Heather; et al. *J Med. Chem.* 1999, 42, 2504–2526) in 120 mL DCM. The reaction was heated under reflux for 16 h, cooled to r.t. and the precipitated product was collected by filtration and dried in vacuum (19.20 g, 54.00 mmol). M.p. 200–202° C.; TLC (PE/EtOAc 1/1) $R_f$ 0.65; $^1$H NMR (400 MHz, D$_6$-DMSO) δ 1.39 (s, 9H); 2.24 (s, 3H); 4.06 (d, J=6 Hz, 2H); 6.93 (mc, 1H); 7.12–7.17 (m, 4); 7.32 (mc, 2H); 7.40 (mc, 2H); 7.85 (mc, 1H); 7.90 (s, 1H); 8.98 (s, 1H).

Example III

N-[4-(Aminomethyl)phenyl]-N'-(2-methylphenyl)urea

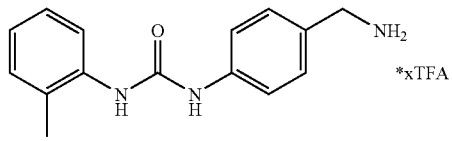

To a solution of tert-butyl 4-({[(2-methylphenyl)amino]carbonyl}amino)benzylcarbamate (2.00 g, 5.63 mmol) in CH$_2$Cl$_2$ (120 mL) TFA (36 mL) was added at 0° C. and stirred for 2 h at r.t.. The reaction mixture was evaporated and the product was collected (2.72 g, TFA salt). M.p. 142–143° C.; TLC (PE/EtOAc 3/2) $R_f$ 0.14; $^1$H NMR (400 MHz, D$_6$-DMSO) δ 2.24 (s, 3H); 3.97 (q, J=5 Hz, 2H); 6.96 (mc, 1H); 7.13–7.19 (m, 2); 7.36 (mc, 2H); 7.51 (mc, 2H); 7.81 (mc, 2H); 8.06 (s, 1H); 8.08 (s, 3H); 9.23 (s, 1H).

Compound Synthesis

Step A:

Example IV tert-Butyl 4-({[1-(3,4-dimethoxyphenyl)-3-ethoxy-3-oxopropyl]-amino}carbonyl benzoate

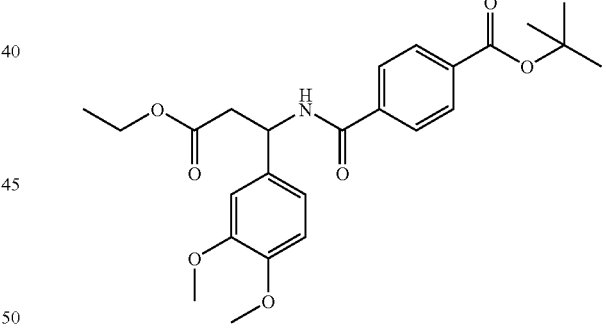

4-(tert-Butoxycarbonyl)benzoic acid (42 mg, 0.19 mmol) was dissolved in MeCN, HOBt (28 mg, 0.21 mmol), EDCI (41 mg, 0.21 mmol), DIPEA (50 μL, 0.29 mmol), and ethyl 3-amino-3-(3,4-dimethoxyphenyl)propanoate*HCl (56 mg, 0.21 mmol) were added at r.t. After stirring for 24 h, the solvent was evaporated and the residue was dissolved in EtOAc (200 mL), washed with 10% aqueous citric acid (50 mL), sat. aqueous soda (50 mL) and dried (NaSO$_4$). The solvent was evaporated in vacuum and the product was collected (47 mg, 0.10 mmol, 53%) as a colorless solid. M.p. 108° C.; TLC (cyclohexane/EtOAc 7/3) $R_f$ 0.17; 1H NMR (400 MHz, CDCl$_3$) δ 1.20 (t, J=7.2 Hz, 3H); 1.26 (mc, 1H); 1.60 (s, 9H); 2.96 (mc, 2H); 3.86 (s, 3H); (s, 3H); 4.12 (q, J=7.1 Hz, 2H); 5.37 (mc, 1H); 6.83 (m, 1H); 6.89 (mc, 1H); 7.55 (mc, 1H); 7.85 (mc, 2H); 8.05 (mc, 2H).

TABLE 1

The following examples were prepared according to the general procedure

| Ex.-No | Structure | Name | M.p. (° C.) |
|---|---|---|---|
| IV | 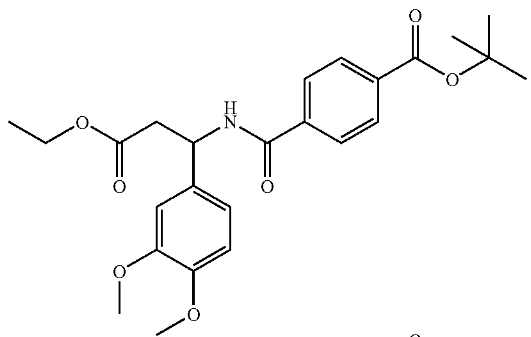 | tert-Butyl 4-({[1-(3,4-di-methoxyphenyl)-3-ethoxy-3-oxopropyl]amino}carbonyl)benzoate | 108 |
| V | 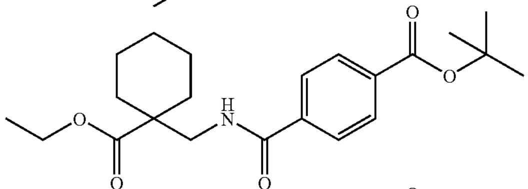 | tert-Butyl 4-[({[1-(ethoxy-carbonyl)cyclohexyl]methyl}-amino)carbonyl]benzoate | 104 |
| VI | 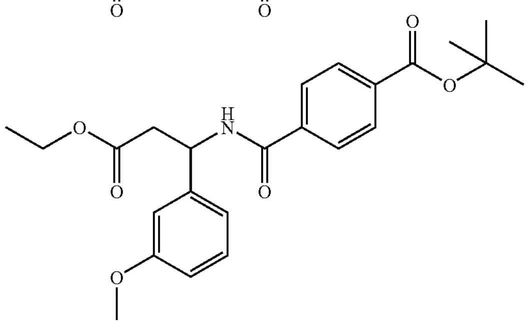 | tert-Butyl 4-({[3-ethoxy-1-(3-methoxyphenyl)-3-oxo-propyl]amino}carbonyl)-benzoate | 102 |

Step B:

Example VII tert-Butyl-4-{[(1-(3,4-dimethoxyphenyl)-3-{[4-({[(2-methylphenyl)-amino]carbonyl}amino)phenyl]amino}-3-oxopropyl)amino]carbonyl}benzoate

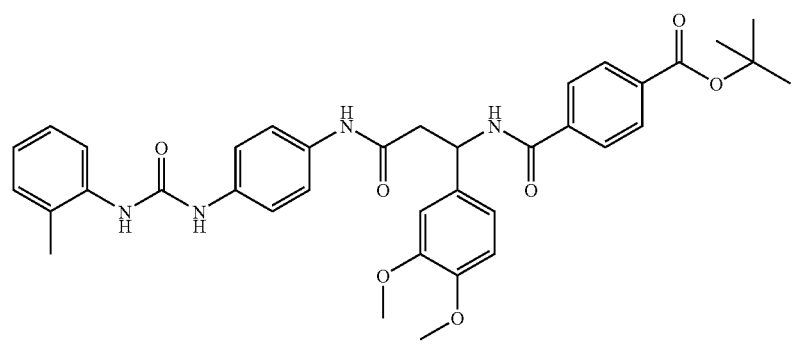

tert-Butyl-4-({[1-(3,4-dimethoxyphenyl)-3-ethoxy-3-oxopropyl]amino}carbonyl)benzoate (40 mg, 0.09 mmol) was dissolved in THF/water (v/v 1/1) and lithium hydroxide (2.3 mg, 0.1 mmol) was added at r.t and the reaction mixture was stirred for 24 h. The solvent was removed under vacuum and the lithium salt of 3-{[4-(tert-butoxycarbonyl)benzoyl]amino}-3-(3,4-dimethoxyphenyl)propanoic acid was isolated (37 mg, 0.09 mmol). The latter compound (18 mg, 0.04 mmol) was dissolved in MeCN (1 mL), HOBt (5.5 mg, 0.05 mmol), EDCI (8.8 mg, 0.05 mmol), and N-(4-aminophenyl)-N'-(2-methylphenyl) urea (10.0 mg, 0.05 mmol) were added. After stirring for 24 h, the solvent was evaporated and the residue was dissolved in EtOAc (200 mL), washed with 10% aqueous citric acid (50 mL), sat. aqueous soda (50 mL) and dried (NaSO$_4$). The solvent was evaporated in vacuum and the product was collected (27 mg, 0.10 mmol, 98%) as a colorless solid. M.p. 210–215° C.; TLC (DCM/MeOH 9/1) R$_f$ 0.21; 1H NMR (400 MHz, D$_6$-DMSO) δ1.56 (s, 9H); 2.23 (s, 3H); 2.86 (mc, 1H); 2.93 (mc, 1H); 3.71 (s, 3H); 3.74 (s, 3H); 5.44 (mc, 1H); 6.88 (mc, 1H); 7.06 (mc, 1H); 7.14 (mc, 1H); 7.36 (mc, 2H); 7.45 (mc, 2H); 7.67 (mc, 1H); 7.81 (mc, 1H); 7.90–8.02 (m, 6H); 9.05 (s, 1H); 9.10 (s, 2H); 9.94 (s, 1H).

TABLE 2

The following examples were prepared according to the general procedure

| Ex.-No. | Structure | Name | M.p. (° C.) |
|---|---|---|---|
| VII | 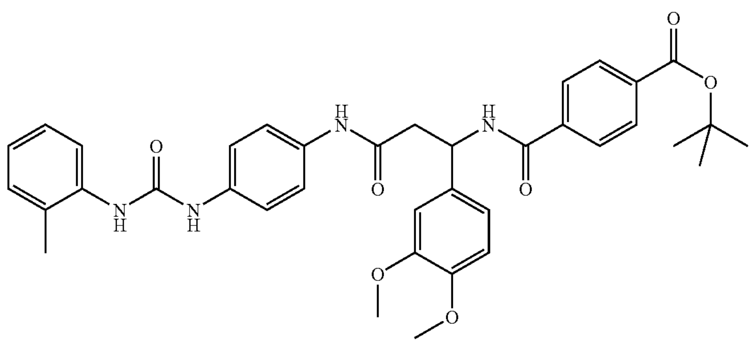 | tert-Butyl 4-{[(1-(3,4-dimethoxyphenyl)-3-{[4-({[(2-methylphenyl)amino]carbonyl}amino)phenyl]-amino}-3-oxopropyl)-amino]carbonyl}benzoate | 210–215 |
| VIII | 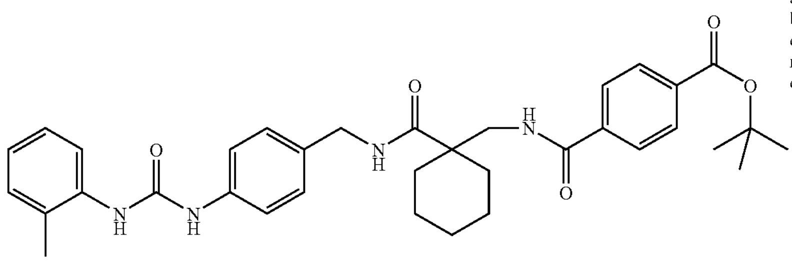 | tert-Butyl 4-[({[1-({[4-({[(2-methylphenyl)amino]carbonyl}amino)benzyl]amino}carbonyl)cyclohexyl]methyl}-amino)carbonyl]benzoate | 187–189 |
| IX | 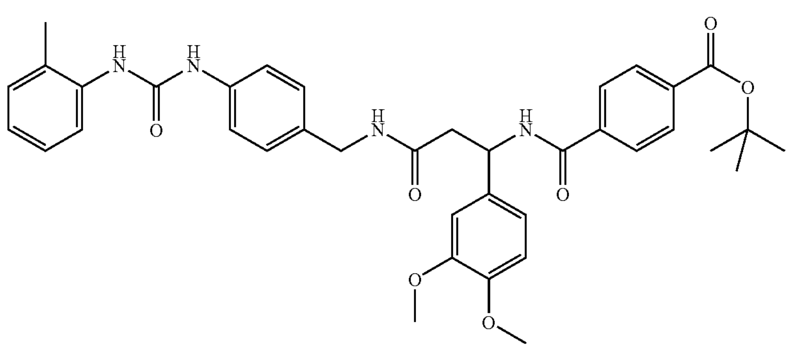 | tert-Butyl-4-{[(1-(3,4-dimethoxyphenyl)-3-{[4-({[(2-methylphenyl)amino]carbonyl}amino)benzyl]amino}-3-oxopropyl)amino]carbonyl}-benzoate | 223–226 |

TABLE 2-continued

The following examples were prepared according to the general procedure

| Ex.-No. | Structure | Name | M.p. (° C.) |
|---|---|---|---|
| X | 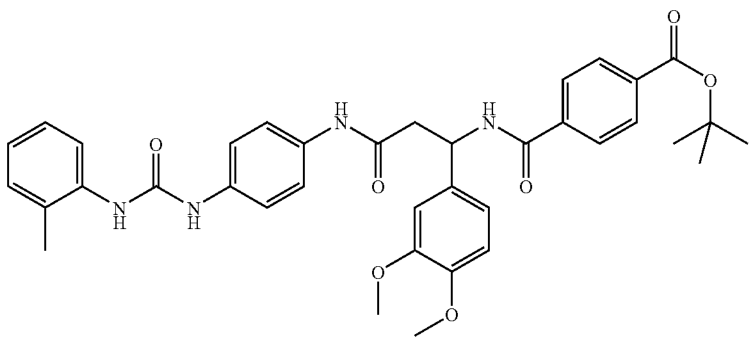 | tert-Butyl 4-{[(1-(3,4-dimethoxyphenyl)-3-{[4-({[(2-methylphenyl)amino]carbonyl}amino)phenyl]amino}-3-oxopropyl)amino]carbonyl}-benzoate | n.d. |

Step C

Example 1

4-{[(1-(3,4-Dimethoxyphenyl)-3-{[4-({[(2-methylphenyl)amino]carbonyl}amino)phenyl]amino}-3-oxopropyl)amino]carbonyl}benzoic acid

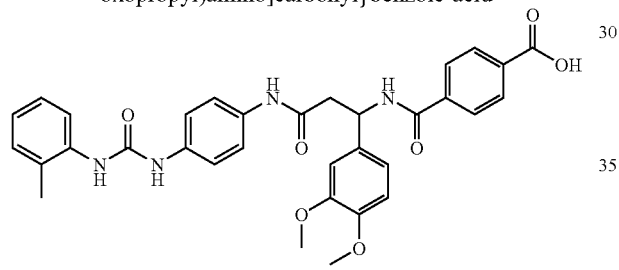

tert-Butyl-4-{[(1-(3,4-dimethoxyphenyl)-3-{[4-({[(2-methylphenyl)amino]carbonyl}amino) phenyl]amino}-3-oxopropyl)amino]carbonyl}benzoate (30 mg, 0.05 mmol) was dissolved in DCM (10 mL) and TFA (0.18 mL, 2.30 mmol) was added at 0° C. and the reaction mixture was stirred at r.t. for 24 h. The solvent was removed in vacuum and the product was isolated (25 mg, 91%). M.p. 166° C. ESI-MS: 598[M+H]$^+$.

TABLE 3

The following examples were prepared according to the general procedure

| No | Structure | Name | M.p. (° C.) |
|---|---|---|---|
| 2 | 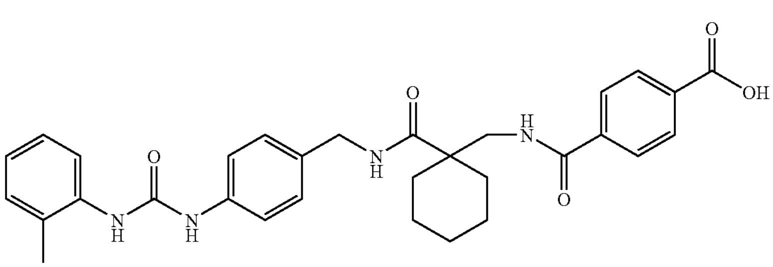 | 4-[({[1-({[4-({[(2-methylphenyl)amino]carbonyl}-amino)benzyl]amino}carbonyl)cyclohexyl]methyl}-amino)carbonyl]benzoic acid | n.d. |

TABLE 3-continued

The following examples were prepared according to the general procedure

| No | Structure | Name | M.p. (° C.) |
|---|---|---|---|
| 3 | 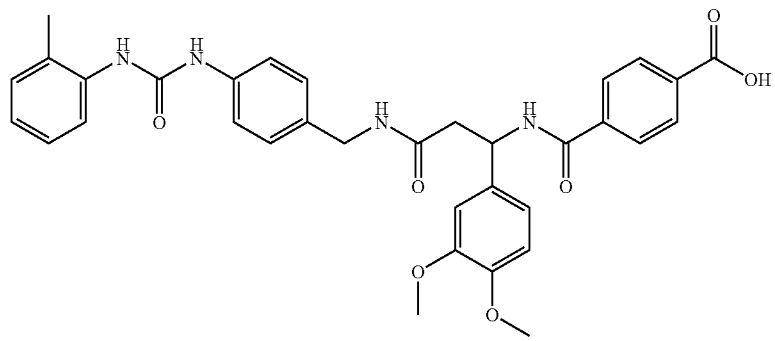 | 4-{[(1-(3,4-dimethoxy-phenyl)-3-{[4-({[(2-methyl-phenyl)amino]carbonyl}amino)benzyl]amino}-3-oxopropyl)amino]carbonyl}benzoic acid | 214 |
| 4 | 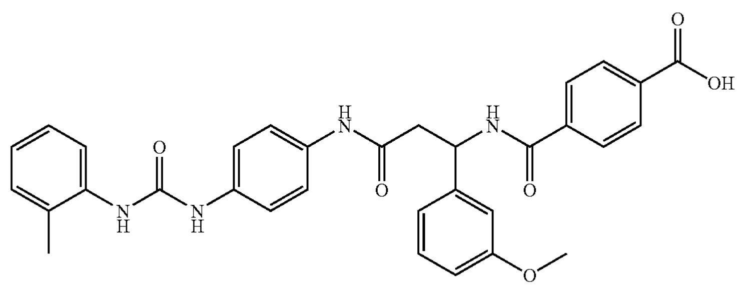 | 4-{[(1-(3-methoxy-phenyl)-3-{[4-({[(2-methylphenyl)-amino]carbonyl}amino)phenyl]amino}-3-oxopropyl)amino]carbonyl}benzoic acid | 275–280 |

In Vitro Assay: Adhesion of Ramos Cells to Immobilized VCAM-1 (Domains 1–3)

Preparation of VCAM-1 (extracellular domains 1–3)

Complementary DNA (cDNA) encoding 7-domain form of VCAM-1 (GenBank accession #M60335) was obtained using Rapid-ScreenTM cDNA library panels (OriGene Technologies, Inc) at Takara Gene Analysis Center (Shiga, Japan). The primers used were 5'-CCA AGG CAG AGT ACG CAA AC-3' (sense) and 5'-TGG CAG GTA TTA TTA AGG AG-3' (antisense). PCR amplification of the 3-domain VCAM-1 cDNA was perform using Pfu DNA polymerase (Stratagene) with the following sets of primers: (U-VCAMd1–3) 5'-CCA TAT GGT ACC TGA TCA ATT TAA AAT CGA GAC CAC CCC AGA A-3'; (L-VCAMd1–3) 5'-CCA TAT AGC AAT CCT AGG TCC AGG GGA GAT CTC AAC AGT AAA-3'. PCR cycle was 94° C. for 45 sec, 55° C. for 45 sec, 72° C. for 2 min, repeating 15 cycles. After the purification of the PCR product, the fragment was digested with KpnI-AvrII. The digested fragment was ligated into pBluescript IISK(-) (Stratagene), which was linearized by digesting with KpnI-XhoI. The ligation was followed by transformation to a Dam/Dcm methylase-free E. coli strain SCS110 (Strategene) to create the donor plasmid pHH7. To direct VCAM-1 molecule into the insect cell secretory pathway, the VCAM-1 coding sequence was fused to signal peptide sequence of honeybee melittin. The resulting melittin-VCAM fusion was placed in correct orientation to the baculovirus polyhedrin promoter. Baculovirus transfer vector containing first 3-domain form VCAM-1 (pH10) was constructed by ligation of 0.9 kb fragment from AvrIIenow/BclI digests of pH7 into SalI/Klenow/BamHI digests of pMelBacB (Invitrogen). Recombinant baculovirus was generated by using Bac-N-Blue™ Transfection kit (Invitrogen) according to the manufacture's instruction. The recombinant virus was amplified by infection to High-Five™ insect cells for 5–6 days, and virus titer was determined by plaque assay.

High-Five™ insect cells were pelleted in a 225 ml conical tube by centrifugation at 1000 rpm for 5 min. After discarding the supernatant, the pellet was resuspended in $1.5 \times 10^9$ pfu (MOI=5) of high-titer virus solution, followed by incubation for 1.5 hours at room temperature. The cells were pelleted again and washed once in fresh Express Five™ serum free medium. The cells were pelleted again and finally, resuspended in 200 ml of fresh Express Five™ medium, transferred to a 1,000 ml shaker flask, and incubated in a shaker at 27° C., 130 rpm, for 48 hours before the culture supernatant was collected. The purification of 3-domain form of VCAM-1 from the culture supernatant was performed by one-step anion exchange chromatography. Protein concentration was determined by using Coomassie protein assay reagent (Pierce) according to the manufacture's instruction.

Preparation of VCAM-1 Coated Microtiter Plates

Recombinant human VCAM-1 (extracellular domains 1–3) was dissolved at 1.0 µg/ml in PBS. Each well of the microtiter plates (Nalge Nunc International, Fluoronunc Cert, 437958) was coated with 100 µl of substrate or for background control with buffer alone for 15 hours at 4 C. After discarding the substrate solution, the wells were blocked using 150 µl per well of block solution (Kirkegaard Perry Laboratories, 50-61-01) for 90 minutes. The plate was washed with wash buffer containing 24 mM Tris-HCl (pH 7.4), 137 mM NaCl, 27 mM KCl and 2 mM $MnCl_2$ just before addition of the assay.

In Vitro Assay Using Ramos Cells

Preparation of Fluorescence Labeled Ramos Cells:

Ramos cells (American Type Culture Collection, Clone CRL-1596) were cultured in RPMI 1640 medium (Nikken Bio Medical Laboratory, CM1101) supplemented with 10% fetal bovine serum (Hyclone, A-1119-L), 100 U/ml penicilin (Gibco BRL, 15140-122) and 100 µg/ml streptomycin (Gibco BRL, 15140-122) in a humidified incubator at 37° C. with 5% $CO_2$.

Ramos cells were incubated with phosphate balanced solution (PBS, Nissui, 05913) containing 25 µM of 5(-and -6)-carboxyfluorescein diacetate, succinimidyle ester (CFSE, Dojindo Laboratories, 345-06441) for 20 min at room temperature while gently swirling every 5 min. After centrifugation at 1000 rpm for 5 min, the cell pellet was resuspended with adhesion assay buffer at a cell density of $4\times10^6$ cells/ml. The adhesion assay buffer was composed of 24 mM Tris-HCl (pH 7.4), 137 mM NaCl, 27 mM KCl, 4 mM glucose, 0.1% bovine serum albumin (BSA, Sigma, A9647) and 2 mM $MnCl_2$.

Assay Procedure (Ramos Cells)

The assay solution containing each test compounds or 5 µg/ml anti-CD49d monoclonal antibody (Immunotech, 0764) was transferred to the VCAM-1 coated plates. The final concentration of each test compounds was 5 µM, 10 µM or various concentrations ranging from 0.0001 µM to 10 µM using a standard 5-point serial dilution. The assay solution containing the labeled Ramos cells was transferred to the VCAM-1 coated plates at a cell density of $2\times10^5$ cells per well and incubated for 1 hour at 37 C. The non-adherent cells were removed by washing the plates 3 times with wash buffer. The adherent cells were broken by addition of 1% Triton X-100 (Nacalai Tesque, 355-01). Released CFSC was quantified fluorescence measurement in a fluorometer (Wallac, ARVO 1420 multilabel counter).

The adhesion of Ramos cells to VCAM-1 was analyzed by percent binding calculated by the formula: 100×(FTS−FBG)/(FTB−FBG)=% binding, where FTB is the total fluorescent intensity from VCAM-1 coated wells without test compound; FBG is the fluorescent intensity from wells with anti-CD49d monoclonal antibody and FTS is the fluorescent intensity from wells containing the test compound of this invention.

In Vitro Activity

In the Ramos VCAM-1 assay the observed $IC_{50}$ value ranges are indicated in Table 4.

C>10 µM≧B>1 µM≧A

TABLE 4

| No | $IC_{50}$ |
|----|-----------|
| 1  | A         |
| 2  | C         |
| 3  | C         |
| 4  | A         |

The invention claimed is:
1. A compound of the general formula (I),

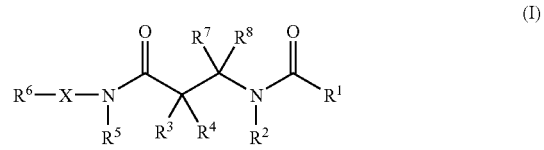

wherein
$R^1$ represents a 4- to 9-membered saturated, unsaturated or aromatic cyclic residue,
and wherein $R^1$ is substituted by —$R^{1-1}$—Z,
wherein
$R^{1-1}$ represents a bond, —O—, —S—, $NR^{1-2}$, $C_1$–$C_{10}$ alkyl, $C_2$–$C_{10}$ alkenyl, $C_2$–$C_{10}$ alkynyl, $C_6$ or $C_{10}$ aryl, or $C_3$–$C_7$ cycloalkyl,
wherein $R^{1-1}$ can optionally be substituted by 1 to 2 substituents selected from the group $R^{1-3}$,
wherein $R^{1-2}$ can optionally be hydrogen, $C_1$–$C_{10}$ alkyl, $C_2$–$C_{10}$ alkenyl or $C_2$–$C_{10}$ alkynyl, and
wherein $R^{1-3}$ represents hydrogen, $C_1$–$C_{10}$ alkyl, $C_2$–$C_{10}$ alkenyl, $C_2$–$C_{10}$ alkynyl, $C_6$ or $C_{10}$ aryl, or $C_3$–$C_7$ cycloalkyl,
Z represents —C(O)$OR^{Z-1}$, —C(O)$NR^{Z-2}R^{Z-3}$, —$SO_2NR^{Z-2}R^{Z-3}$, —SO($OR^{Z-1}$), —$SO_2$($OR^{Z-1}$), —P(O)$R^{Z-1}$($OR^{Z-3}$) or —PO($OR^{Z-1}$)($OR^{Z-3}$),
wherein $R^{Z-2}$ is hydrogen, $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl, —C(O)$R^{Z-4}$ or —$SO_2R^{Z-4}$,
wherein $R^{Z-4}$ is $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl,
$R^{Z-1}$ and $R^{Z-3}$ are independently selected from the group hydrogen, $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl or benzyl,
wherein $R^{Z-1}$ and $R^{Z-3}$ can optionally be substituted by 1 to 3 substituents selected from the group $C_1$–$C_4$ alkyl, $C_1$–$C_4$ alkyloxy, halogen, nitro, and cyano,
and wherein $R^1$ can optionally be substituted by 0 to 2 substituents selected from $R^{1-4}$, halogen, nitro, amino, cyano and oxo,
wherein
$R^{1-4}$ is selected from the group $C_1$–$C_4$ alkyl, $C_1$–$C_4$ alkyloxy, phenyl, phenoxy, phenylamino, and $C_3$–$C_6$ cycloalkyl,
$R^2$ represents hydrogen, $C_1$–$C_{10}$ alkyl, $C_2$–$C_{10}$ alkenyl, $C_2$–$C_{10}$ alkynyl, $C_6$ or $C_{10}$ aryl or $C_3$–$C_7$ cycloalkyl,
wherein $R^2$ can optionally be substituted by 1 to 3 radicals independently selected from the group $C_1$–$C_4$ alkyl, trifluormethyl, trifluormethoxy, halogen, cyano, nitro and oxo,
$R^3$ represents hydrogen, $C_1$–$C_{10}$ alkyl, $C_2$–$C_{10}$ alkenyl, $C_2$–$C_{10}$ alkynyl, $C_6$ or $C_{10}$ aryl, or $C_3$–$C_7$ cycloalkyl,
wherein $R^3$ can optionally be substituted by 1 to 3 radicals $R^{3-1}$,
wherein $R^{3-1}$ represents $C_1$–$C_4$ alkyl, trifluormethyl, trifluormethoxy, —$OR^{3-2}$, —$SR^{3-2}$, $NR^{3-3}R^{3-4}$, —C(O)$R^{3-2}$, S(O)$R^{3-2}$, —$SO_2R^{3-2}$, —OC(O)$R^{3-2}$, —C(O)$NR^{3-3}R^{3-4}$, —$NR^{3-2}$C(O)$R^{3-3}$, —$SO_2NR^{3-3}R^{3-4}$, $NR^{3-2}SO_2R^{3-3}$, —$NR^{3-2}$C(O)$NR^{3-3}R^{3-4}$, —$NR^{3-2}$C(O)$OR^{3-3}$, —OC(O)$NR^{3-3}R^{3-4}$, —$CO_2R^{3-5}$, halogen, cyano, nitro or oxo,
wherein $R^{3-2}$ represents hydrogen, $C_1$–$C_4$ alkyl, $C_3$–$C_6$ cycloalkyl, $C_6$ or $C_{10}$ aryl, wherein $R^{3-3}$ and $R^{3-4}$ are independently selected from the group hydrogen, $C_1$–$C_4$ alkyl, $C_3$–$C_6$ cycloalkyl, $C_6$ or $C_{10}$ aryl and benzyl, and wherein $R^{3-5}$ represents $C_1$–$C_4$ alkyl, $C_3$–$C_6$ cycloalkyl, $C_6$ or $C_{10}$ aryl, $R^4$ represents hydrogen, $C_1$–$C_{10}$ alkyl, $C_2$–$C_{10}$ alkenyl, $C_2$–$C_{10}$alkynyl, $C_6$ or $C_{10}$ aryl, or $C_3$–$C_7$ cycloalkyl, wherein $R^4$ can optionally be substituted by 1 to 3 radicals $R^{4-1}$, wherein $R^{4-1}$ represents $C_1$–$C_4$ alkyl, trifluormethyl, trifluormethoxy, —$OR^{4-2}$, —$SR^{4-2}$, —$NR^{4-3}R^{4-4}$, —C(O)$R^{4-2}$, $S(O)R^{4-2}$, —$SO_2R^{4-2}$, —$OC(O)R^{4-2}$, —C(O)$NR^{4-3}R^{4-4}$, —$NR^{4-2}C(O)R^{4-3}$, —$SO_2NR^{4-3}R^{4-4}$, $NR^{4-2}SO_2R^{4-3}$, —$NR^{4-2}C(O)NR^{4-3}R^{4-4}$, —$NR^{4-2}C(O)OR^{4-3}$, —$OC(O)NR^{4-3}R^{4-4}$, —$CO_2R^{4-5}$, halogen, cyano, nitro or oxo, wherein $R^{4-2}$ represents hydrogen, $C_1$–$C_4$ alkyl, $C_3$–$C_6$ cycloalkyl, $C_6$ or $C_{10}$ aryl, wherein $R^{4-3}$ and $R^{4-4}$ are independently selected from the group hydrogen, $C_1$–$C_4$ alkyl, $C_3$–$C_6$ cycloalkyl, $C_6$ or $C_{10}$ aryl and benzyl, and wherein $R^{4-5}$ represents $C_1$–$C_4$ alkyl, $C_3$–$C_6$ cycloalkyl, $C_6$ or $C_{10}$ aryl $R^5$ represents hydrogen, $C_1$–$C_{10}$ alkyl, $C_2$–$C_{10}$ alkenyl, $C_2$–$C_{10}$ alkynyl, $C_6$ or $C_{10}$ aryl or $C_3$–$C_7$ cycloalkyl, wherein $R^5$ can optionally up to threefoldedly be substituted by $C_1$–$C_4$ alkyl, trifluormethyl, trifluormethoxy, halogen, cyano, nitro or oxo, $R^6$ represents phenyl, which is substituted by —$NR^{6-2}C(O)NR^{6-3}R^{6-4}$ or —$NR^{6-2}C(S)NR^{6-3}R^{6-4}$ and can furthermore optionally be substituted by halogen, wherein $R^{6-2}$ and $R^{6-3}$ are independently selected from the group hydrogen and $C_1$–$C_4$ alkyl, or together form a group

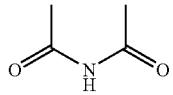

and wherein $R^{6-4}$ represents phenyl, wherein $R^{6-4}$ can optionally be substituted by 1–2 substituents selected from the group $C_1$–$C_4$ alkyl, $C_1$–$C_4$ alkyloxy, halogen, nitro, trifluoromethyl, trifluoromethoxy and cyano, $R^7$ represents hydrogen, $C_1$–$C_{10}$ alkyl, $C_2$–$C_{10}$ alkenyl, $C_2$–$C_{10}$ alkynyl, $C_6$ or $C_{10}$ aryl, or $C_3$–$C_7$ cycloalkyl, wherein $R^7$ can optionally be substituted by 1 to 3 radicals $R^{7-1}$, wherein $R^{7-1}$ represents $C_1$–$C_4$ alkyl, trifluormethyl, trifluormethoxy, —$OR^{7-2}$, —$SR^{7-2}$, —$NR^{7-3}R^{7-4}$, —C(O)$R^{7-2}$, $S(O)R^{7-2}$, —$SO_2R^{7-2}$, —$OC(O)R^{7-2}$, —C(O)$NR^{7-3}R^{7-4}$, —$NR^{7-2}C(O)R^{7-3}$, —$SO_2NR^{7-3}R^{7-4}$, $NR^{7-2}SO_2R^{7-3}$, —$NR^{7-2}C(O)NR^{7-3}R^{7-4}$, —$NR^{7-2}C(O)OR^{7-3}$, —$OC(O)NR^{7-3}R^{7-4}$, —$CO_2R^{7-5}$, halogen, cyano, nitro or oxo, wherein $R^{7-2}$ represents hydrogen, $C_1$–$C_4$ alkyl, $C_3$–$C_6$ cycloalkyl, $C_6$ or $C_{10}$ aryl, wherein $R^{7-3}$ and $R^{7-4}$ are independently selected from the group hydrogen, $C_1$–$C_4$ alkyl, $C_3$–$C_6$ cycloalkyl, $C_6$ or $C_{10}$ aryl and benzyl, and wherein $R^{7-5}$ represents $C_1$–$C_4$ alkyl, $C_3$–$C_6$ cycloalkyl, $C_6$ or $C_{10}$ aryl $R^8$ represents hydrogen, $C_1$–$C^{10}$ alkyl, $C_2$–$C_{10}$ alkenyl, $C_2$–$C_{10}$ alkynyl, $C_6$ or $C_{10}$ aryl, or $C_3$–$C_7$ cycloalkyl, wherein $R^8$ can optionally be substituted by 1 to 3 radicals $R^{8-1}$, wherein $R^{8-1}$ represents $C_1$–$C_4$ alkyl, trifluormethyl, trifluormethoxy, —$OR^{8-2}$, —$SR^{8-2}$, —$NR^{8-3}R^{8-4}$, —C(O)$R^{8-2}$, $S(O)R^{8-2}$, —$SO_2R^{8-2}$, —$OC(O)R^{8-2}$, —C(O)$NR^{8-3}R^{8-4}$, —$NR^{8-2}C(O)R^{8-3}$, —$SO_2NR^{8-3}R^{8-4}$, $NR^{8-2}SO_2R^{8-3}$, —$NR^{8-2}C(O)NR^{8-3}R^{8-4}$, —$NR^{8-2}C(O)OR^{8-3}$, —$OC(O)NR^{8-3}R^{8-4}$, —$CO_2R^{8-5}$, halogen, cyano, nitro or oxo, wherein $R^{8-2}$ represents hydrogen, $C_1$–$C_4$ alkyl, $C_3$–$C_6$ cycloalkyl, $C_6$ or $C_{10}$ aryl, wherein $R^{8-3}$ and $R^{8-4}$ are independently selected from the group hydrogen, $C_1$–$C_4$ alkyl, $C_3$–$C_6$ cycloalkyl, $C_6$ or $C_{10}$ aryl and benzyl, and wherein $R^{8-5}$ represents $C_1$–$C_4$ alkyl, $C_3$–$C_6$ cycloalkyl, or $C_6$ or $C_{10}$ aryl X represents bond or (—$CR^{X-1}R^{X-2}$—)$_n$, wherein $R^{X-1}$ and $R^{X-2}$ can be independently selected from the group hydrogen, $C_1$–$C_4$ alkyl, $C_2$–$C_4$ alkenyl, and $C_2$–$C_4$ alkynyl, wherein $R^{X-1}$ and $R^{X-2}$ can optionally independently be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, and oxo, and wherein n is an integer 0 or 1 or a pharmaceutically acceptable salt thereof.

2. The compound of general formula (I) according to claim 1, wherein $R^1$ represents a phenyl ring.

3. The compound according to claim 1 or 2, wherein $R^{1-1}$ represents a bond and Z represents COO$R^{Z-1}$, wherein $R^{Z-1}$ has the meaning indicated in claim 1.

4. The compound according to claim 1, wherein $R^6$ represents phenyl, which is substituted by —NHC(O)NH$R^{6-4}$, wherein $R^{6-4}$ is substituted with methyl or trifluoromethoxy.

5. The compound according to claim 1, wherein $R^{X-1}$ and $R^{X-2}$ represent hydrogen.

6. The compound according to claim 1, wherein $R^3$ and $R^3$ together form a 6-membered homocycle.

7. The compound according to claim 1, wherein $R^3$, $R^4$ and $R^7$ represent hydrogen and $R^8$ represents a 3-methoxyphenyl radical or a 3,4-dimethoxyphenyl radical.

8. The compound of general formula (I) according to claim 2, characterized in that $R^1$ is a 1,4-substituted phenyl ring.

9. A process for preparation of compounds of general formula (I) according to claim 1, which comprises reacting a carboxylic acid of general formula (I')

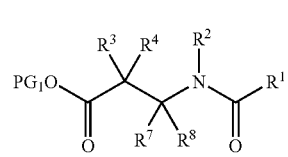

or an activated derivative thereof, wherein PG$_1$ represents a protecting group, and $R^1$, $R^2$, $R^3$, $R^4$, $R^7$, and $R^8$ have the meanings shown in claim 1, with a compound of the general formula (I″)

$$R^6\text{—}X\text{—}NR^5H \quad (I'')$$

wherein $R^5$, $R^6$, and X have the meanings shown in claim 1,
in inert solvent.

10. A method for the treatment of a condition selected from the group consisting of atherosclerosis, asthma, chronic obstructive pulmonary disease (COPD), allergies, diabetes, inflammatory bowel disease, multiple sclerosis, myocardial ischemia, rheumatoid arthritis, and transplant rejection, comprising administering to a subject in need thereof an effective amount of a compound according to claim 1.

11. A pharmaceutical composition, comprising a compound according to claim 1 and a pharmaceutically acceptable carrier.

* * * * *